(12) United States Patent
Iwakawa et al.

(10) Patent No.: US 12,343,189 B2
(45) Date of Patent: Jul. 1, 2025

(54) X-RAY INSPECTION APPARATUS AND ADJUSTMENT METHOD THEREOF

(71) Applicant: ISHIDA CO., LTD., Kyoto (JP)

(72) Inventors: Ken Iwakawa, Ritto (JP); Futoshi Yurugi, Ritto (JP); Keisuke Yoshida, Ritto (JP)

(73) Assignee: ISHIDA CO., LTD., Kyoto (JP)

( * ) Notice: Subject to any disclaimer, the term of this patent is extended or adjusted under 35 U.S.C. 154(b) by 210 days.

(21) Appl. No.: 18/167,831

(22) Filed: Feb. 10, 2023

(65) Prior Publication Data

US 2023/0284991 A1 Sep. 14, 2023

(30) Foreign Application Priority Data

Mar. 11, 2022 (JP) .................. 2022-037999

(51) Int. Cl.
*A61B 6/40* (2024.01)
*A61B 6/00* (2006.01)

(52) U.S. Cl.
CPC ............ *A61B 6/482* (2013.01); *A61B 6/4035* (2013.01)

(58) Field of Classification Search
CPC .............................. A61B 6/482; A61B 6/4035
See application file for complete search history.

(56) References Cited

U.S. PATENT DOCUMENTS

| | | | | |
|---|---|---|---|---|
| 7,037,735 B2 * | 5/2006 | Noguchi | .......... | G01N 21/95623 438/18 |
| 2010/0202584 A1 * | 8/2010 | Wang | .................. | G01N 23/087 378/53 |
| 2014/0326894 A1 * | 11/2014 | Abraham | ................. | H04N 5/32 250/394 |
| 2015/0342549 A1 * | 12/2015 | Kwon | .................... | A61B 6/469 378/37 |
| 2017/0269257 A1 * | 9/2017 | Scoullar | ................. | G01V 5/224 |
| 2017/0365077 A1 * | 12/2017 | Monkawa | ........... | H04N 13/204 |

(Continued)

FOREIGN PATENT DOCUMENTS

| | | |
|---|---|---|
| CN | 108254394 B | 9/2020 |
| JP | 6569070 B2 | 9/2019 |
| WO | 2018/066364 A1 | 4/2018 |

OTHER PUBLICATIONS

Extended Search Report in the corresponding European Patent Application No. 23153864.6 dated May 26, 2023.

*Primary Examiner* — Hugh Maupin
(74) *Attorney, Agent, or Firm* — Global IP Counselors, LLP

(57) ABSTRACT

An X-ray inspection apparatus includes: a transport unit configured to transport an article; an X-ray source configured to irradiate the article with X-rays; an X-ray detection unit configured to detect the X-rays using a photon counting method and to classify photon energy of the detected X-rays into two or more energy regions on the basis of a threshold value; a threshold value setting unit configured to set the threshold value; an X-ray image generation unit configured to generate two or more X-ray transmission images corresponding to the two or more energy regions on the basis of a detection result of the X-rays; and an inspection unit configured to inspect the article on the basis of the X-rays. The threshold value setting unit is configured to set the threshold value on the basis of gradations of the two or more X-ray transmission images.

15 Claims, 8 Drawing Sheets

(56) References Cited

U.S. PATENT DOCUMENTS

| | | | |
|---|---|---|---|
| 2018/0243800 A1* | 8/2018 | Kumar | G06N 20/00 |
| 2023/0122223 A1* | 4/2023 | Takata | G01N 23/04 |
| | | | 382/110 |
| 2024/0212163 A1* | 6/2024 | Yang | G06T 7/13 |

* cited by examiner

X-RAY INSPECTION APPARATUS AND ADJUSTMENT METHOD THEREOF

TECHNICAL FIELD

The present disclosure relates to an X-ray inspection apparatus and an adjustment method thereof.

BACKGROUND

For example, an apparatus described in Japanese Patent No. 6569070 is known as an X-ray inspection apparatus according to the related art. The X-ray inspection apparatus described in Japanese Patent No. 6569070 includes an X-ray detection means for classifying the energy of each photon of X-rays, which have been transmitted through an object to be measured, into two or more energy regions according to a predetermined number of energy threshold values and detecting the photons, a storage means in which each of a plurality of types of objects to be measured and the energy threshold values are stored so as to be directly or indirectly associated with each other, a threshold setting means for holding the threshold value corresponding to the object to be measured, whose type has been specified by input information, such that the X-ray detection means can refer to the threshold value as a predetermined threshold value, an inspection means for inspecting the object to be measured on the basis of the number of photons detected by the X-ray detection means for each of one or more energy regions or an amount corresponding to the number of photons.

SUMMARY

In the above-described X-ray inspection apparatus, it is possible to use the energy threshold value that is stored in advance by the storage means and that corresponds to the physical properties of an article which is the object to be measured. However, in some cases, the energy threshold value stored in advance is not optimal depending on, for example, the inspection conditions of the article (for example, the transport speed of the object to be measured and the like), a variation in the performance of the X-ray inspection apparatus, and the state of the X-ray inspection apparatus (for example, a change in energy distribution due to deterioration of an X-ray source). Therefore, in some cases, the accuracy of inspecting the object to be measured is reduced depending on, for example, the inspection conditions.

An object of an aspect of the present disclosure is to provide an X-ray inspection apparatus that can inspect an article with high accuracy even when inspection conditions of the article and the like are changed and an adjustment method thereof.

According to an aspect of the present disclosure, there is provided an X-ray inspection apparatus including: a transport unit configured to transport an article; an X-ray source configured to irradiate the article with X-rays; an X-ray detection unit configured to detect the X-rays using a photon counting method and to classify photon energy of the detected X-rays into two or more energy regions on the basis of a threshold value; a threshold value setting unit configured to set the threshold value; an X-ray image generation unit configured to generate two or more X-ray transmission images corresponding to the two or more energy regions on the basis of a detection result of the X-rays by the X-ray detection unit; and an inspection unit configured to inspect the article on the basis of the X-rays which have been transmitted through the article and detected by the X-ray detection unit. The threshold value setting unit is configured to set the threshold value on the basis of gradations of the two or more X-ray transmission images.

According to another aspect of the present disclosure, there is provided an X-ray inspection apparatus including: a transport unit configured to transport an article; an X-ray source configured to irradiate the article with X-rays; an X-ray detection unit configured to detect the X-rays using a photon counting method; and a control unit to which a detection result of the X-ray detection unit is input. The control unit includes: a classification unit configured to classify photon energy of the X-rays detected by the X-ray detection unit into two or more energy regions on the basis of a threshold value; a threshold value setting unit configured to set the threshold value; an X-ray image generation unit configured to generate two or more X-ray transmission images corresponding to the two or more energy regions on the basis of the detection result of the X-rays by the X-ray detection unit; and an inspection unit configured to inspect the article on the basis of the X-rays which have been transmitted through the article and detected by the X-ray detection unit. The threshold value setting unit is configured to set the threshold value on the basis of gradations of the two or more X-ray transmission images.

According to these X-ray inspection apparatuses, the threshold value setting unit is configured to set the threshold value on the basis of the gradations of two or more X-ray transmission images. Therefore, in some cases, for example, when the inspection conditions of the article are changed, the threshold value is changed. That is, the threshold value setting unit can set an appropriate threshold value corresponding to a change in the inspection conditions and the like, Therefore, even when the inspection conditions of the article and the like are changed, it is possible to inspect the article with high accuracy.

The X-ray detection unit or the classification unit may classify the photon energy into a first energy region, a second energy region, and a third energy region lower than the first energy region and the second energy region. In this case, for example, an energy region including the largest amount of noise among the first to third energy regions can be excluded to improve the accuracy of inspecting the article.

The threshold value may be determined on the basis of a second threshold value at which a difference between the gradations of the two or more X-ray transmission images is within a predetermined range. In this case, it is easy to find out, for example, whether or not a foreign material is present or absent in the article.

The threshold value may be a value obtained by adding a correction value to the second threshold value. In this case, it is possible to improve the accuracy of inspecting the article.

When the difference between the gradations of the two or more X-ray transmission images is out of the predetermined range, after the threshold value setting unit changes the threshold value, the X-ray image generation unit may generate two or more second X-ray transmission images corresponding to two or more fourth energy regions classified on the basis of the changed threshold value, and the threshold value setting unit may determine whether or not a difference between gradations of the second X-ray transmission images is within a predetermined range. In this case, the threshold value setting unit can accurately set the threshold value at which the difference between the gradations of the two or more X-ray transmission images is within a predetermined range.

The X-ray image generation unit may generate two or more second X-ray transmission images corresponding to two or more fourth energy regions classified on the basis of a third threshold value different from the threshold value, and the threshold value setting unit may compare the difference between the gradations of the two or more X-ray transmission images with a difference between gradations of the second X-ray transmission images. In this case, the threshold value setting unit can easily determine whether or not the threshold value is appropriate on the basis of the comparison between the differences.

According to still another aspect of the present disclosure, there is provided an adjustment method of an X-ray inspection apparatus. The adjustment method includes: an X-ray irradiation step of irradiating an inspection room provided in a housing with X-rays; an X-ray detection step of detecting the X-rays using a photon counting method; a classification step of classifying photon energy of the detected X-rays into two or more energy regions on the basis of a threshold value; an image generation step of generating two or more X-ray transmission images corresponding to the two or more energy regions, using the photon energy; and a threshold value setting step of setting the threshold value on the basis of gradations of the two or more X-ray transmission images.

According to this adjustment method, in the threshold value setting step, the threshold value is set on the basis of the gradations of two or more X-ray transmission images. Therefore, in some cases, for example, when the inspection conditions of the article are changed, the threshold value is changed. That is, the threshold value can be changed to an appropriate threshold value corresponding to a change in the inspection conditions and the like, Therefore, according to the X-ray inspection apparatus in which this adjustment method is performed, even when the inspection conditions of the article and the like are changed, it is possible to inspect the article with high accuracy.

When a difference between the gradations of the two or more X-ray transmission images is out of a predetermined range in the threshold value setting step, a change of the threshold value, the classification step, the image generation step, and the threshold value setting step may be performed until the difference falls within the predetermined range. In this case, it is possible to accurately set the threshold value at which the difference between the gradations of two or more X-ray transmission images is within the predetermined range.

In the classification step, the photon energy may be classified into two or more second energy regions on the basis of a second threshold value different from the threshold value. In the image generation step, two or more second X-ray transmission images corresponding to the second energy regions may be generated. In the threshold value setting step, a difference between the gradations of the X-ray transmission images may be compared with a difference between gradations of the second X-ray transmission images. In this case, it is easily possible to determine whether or not the threshold value is appropriate on the basis of the comparison between the differences.

According to an aspect of the present disclosure, it is possible to provide an X-ray inspection apparatus that can inspect an article with high accuracy even when inspection conditions of the article and the like are changed and an adjustment method thereof.

DETAILED DESCRIPTION

Figure 1:
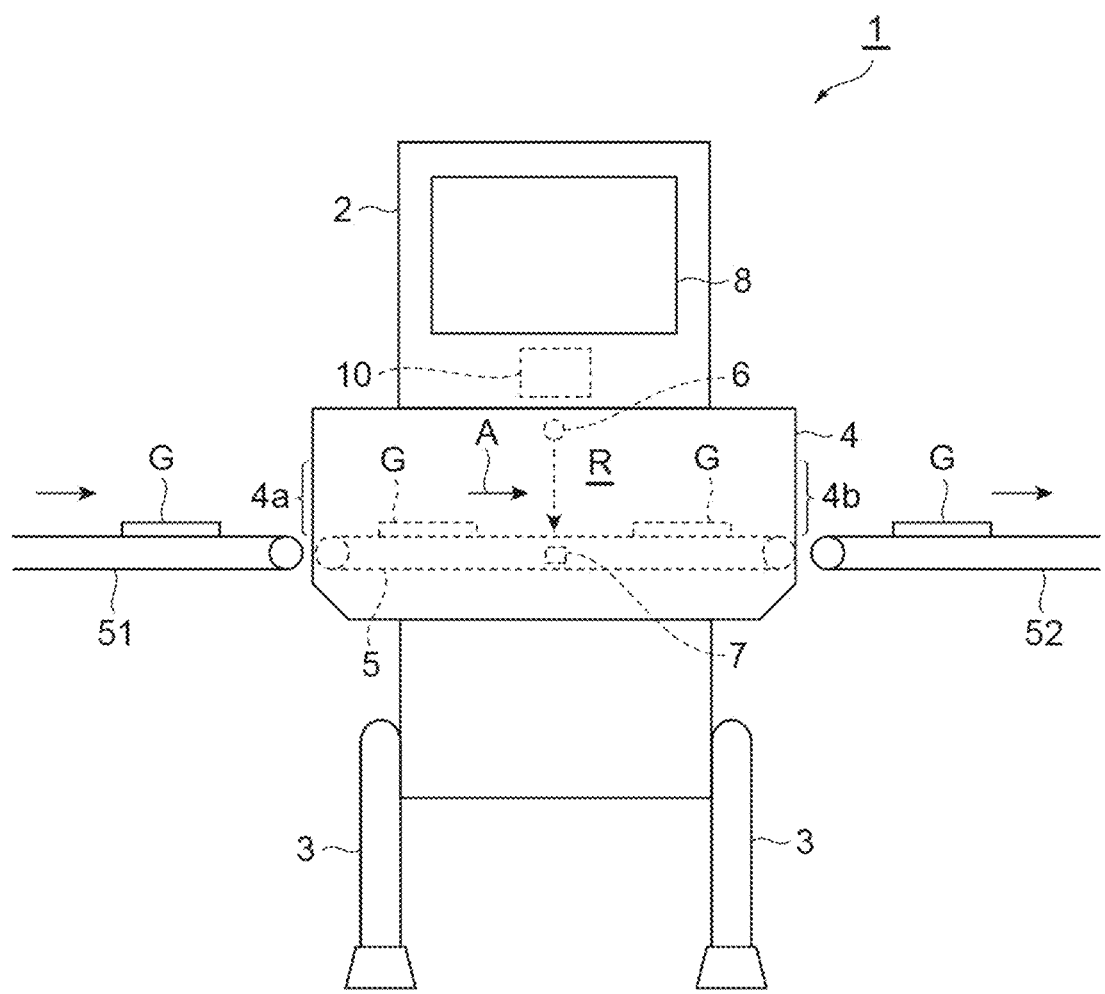
FIG. 1 is a diagram showing a configuration of an X-ray inspection apparatus according to an embodiment.

Hereinafter, a preferred embodiment of the present disclosure will be described in detail with reference to the accompanying drawings. In addition, in the description of the drawings, the same or corresponding elements are denoted by the same reference numerals, and the redundant description thereof will be omitted.

As shown in FIG. 1, an X-ray inspection apparatus 1 includes an apparatus main body 2, support legs 3, a shield box 4, a transport unit 5, an X-ray irradiation unit 6, an X-ray detection unit 7, a display operation unit 8, and a control unit 10. The X-ray inspection apparatus 1 generates an X-ray transmission image of an article G while transporting the article G and inspects the article G on the basis of the X-ray transmission image. The article G before inspection is carried into the X-ray inspection apparatus 1 by a carry-in conveyor 51. The article U after inspection is carried out from the X-ray inspection apparatus 1 by a carry-out conveyor 52. The article G determined to be defective by the X-ray inspection apparatus 1 is sorted out of a production line by a sorting device (not shown) that is disposed on a downstream side of the carry-out conveyor 52. The article G determined to be non-defective by the X-ray inspection apparatus 1 passes through the sorting device as it is. In this embodiment, the article G is a cereal flake.

The apparatus main body 2 accommodates the control unit 10 and the like. The support legs 3 support the apparatus main body 2. The shield box 4 is provided in the apparatus main body 2. The shield box 4 is a housing that prevents the leakage of X-rays (electromagnetic waves) to the outside. An inspection room R in which the article G is inspected by X-rays is provided in the shield box 4. A carry-in port 4a and a carry-out port 4b are formed in the shield box 4. The article G before inspection is carried from the carry-in conveyor 51 into the inspection room R through the carry-in port 4a. The article G after inspection is carried out from the inspection room R to the carry-out conveyor 52 through the carry-out port 4b. An X-ray shielding curtain (not shown) that prevents the leakage of X-rays is provided in each of the carry-in port 4a and the carry-out port 4b.

The transport unit 5 is a member that transports the article G and is disposed so as to pass through the center of the shield box 4. The transport unit 5 transports the article G along a transport direction A from the carry-in port 4a to the carry-out port 4b through the inspection room R. The transport unit 5 is, for example, a belt conveyor that extends between the carry-in port 4a and the carry-out port 4b. In addition, the transport unit 5, which is a belt conveyor, may protrude from the carry-in port 4a and the carry-out port 4b to the outside.

Figure 2:
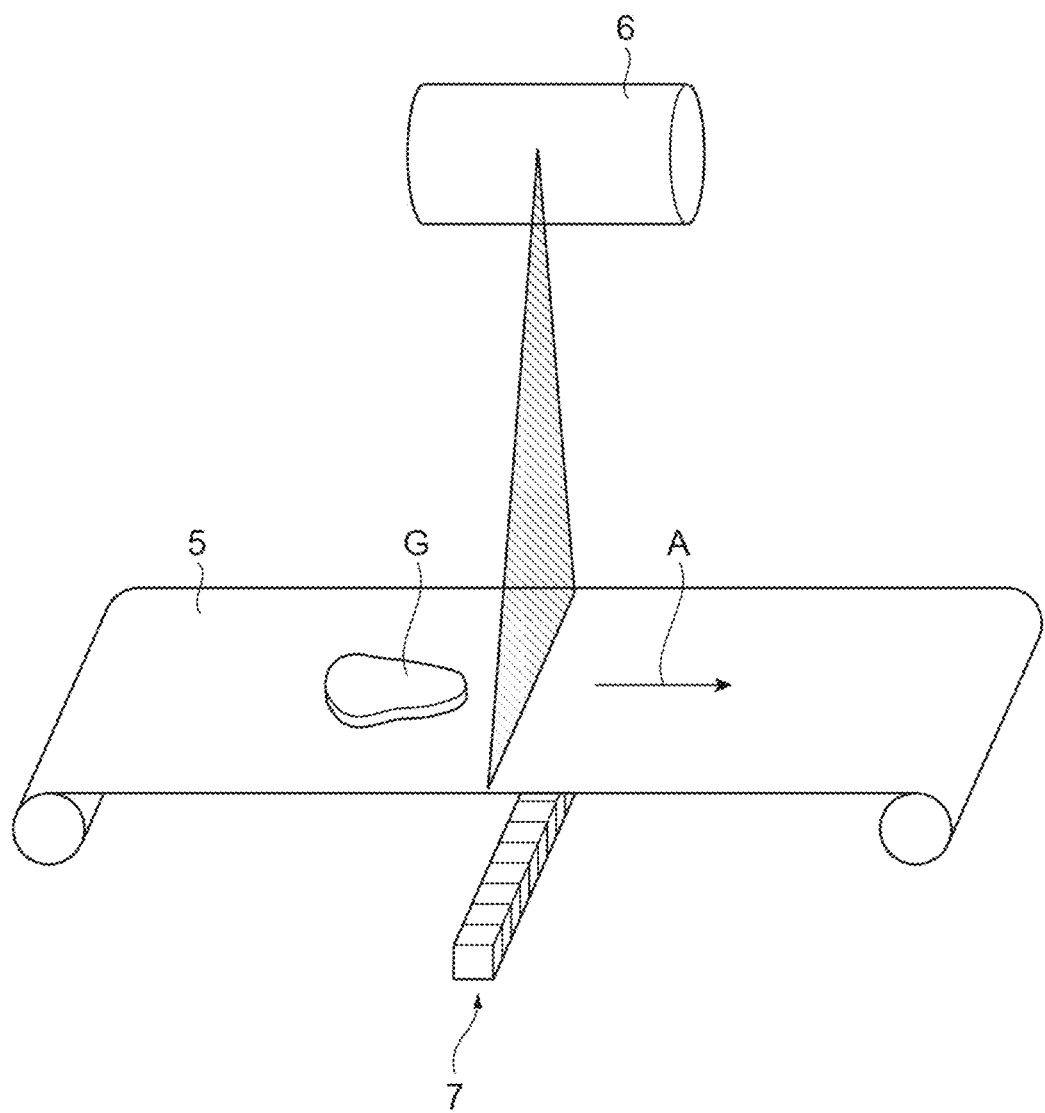
FIG. 2 is a diagram showing an internal configuration of a shield box shown in FIG. 1.

As shown in FIGS. 1 and 2, the X-ray irradiation unit 6 is an electromagnetic wave irradiation unit (X-ray source) that is disposed in the shield box 4. The X-ray irradiation unit 6 has, for example, an X-ray tube that emits X-rays and a collimator unit that spreads the X-rays emitted from the X-ray tube in a fan shape in a plane perpendicular to the transport direction A. The X-rays emitted from the X-ray irradiation unit 6 include X-rays in various energy regions from low energy (long wavelength) to high energy (short wavelength). Therefore, the X-ray irradiation unit 6 irradiates the article G transported by the transport unit 5 with X-rays in a plurality of energy regions. In addition, "low" and "high" in the low energy and the high energy described above indicate relatively "low" and "high" among a plurality of energy regions of X-rays emitted from the X-ray irradiation unit 6 and do not indicate a specific range.

The X-ray detection unit 7 is a sensor member that detects electromagnetic waves. The X-ray detection unit 7 is disposed in the shield box 4 at a position facing the X-ray irradiation unit 6 in the vertical direction. The X-ray detection unit 7 may be capable of detecting X-rays in a specific energy region or may be capable of detecting X-rays using a photon counting method. The X-ray detection unit 7 may be a direct-conversion-type detection unit or an indirect-conversion-type detection unit. In this embodiment, the X-ray detection unit 7 is a direct-conversion-type detection unit that can detect X-rays using the photon counting method and includes, for example, a sensor (multi-energy sensor) that detects X-rays in each of a plurality of energy regions transmitted through the article G. The sensor includes elements that are arranged, for example, in a direction (width direction) orthogonal to at least the transport direction of the transport unit 5 and the vertical direction. The elements may be arranged not only in the width direction but also in the transport direction. That is, the X-ray detection unit 7 may include a line sensor or may include a group of sensors that are arranged two-dimensionally. The sensor is, for example, a photon-detection-type sensor such as a CdTe semiconductor detector.

In the element included in the X-ray detection unit 7, fir example, electron-hole pairs are generated by the arrival of X-ray photons. Photon counting is performed on the basis of the energy (photon energy) obtained at this time.

The X-ray detection unit 7 classifies the photon energy of the detected X-rays into two or more energy regions on the basis of an arbitrary threshold value. This enables the X-ray detection unit 7 to perform photon counting for each energy region. The X-ray detection unit 7 outputs a divided signal (detection result signal) corresponding to the detection result of the X-rays to the control unit 10. In this embodiment, the X-ray detection unit 7 divides the photon energy of the detected X-rays into at least a first energy region and a second energy region higher than the first energy region, using the arbitrary threshold value. The arbitrary threshold value is, for example, one or more values (unit: keV) set by the control unit 10. Therefore, the first energy region and the second energy region may be divided by one threshold value or different threshold values (fir example, a first threshold value and a second threshold value different from the first threshold value). In the latter case, one or more energy regions may be present between the first energy region and the second energy region. For example, the X-ray detection unit 7 may classify the photon energy into the first energy range, the second energy range, and a third energy range lower than the first energy range and the second energy range. The arbitrary threshold value and the number thereof can be appropriately confirmed through the display operation unit 8 according to, for example, a change in the type of the article U and a change in inspection conditions. In addition, a method for setting the arbitrary threshold value will be described below.

As shown in FIG. 1, the display operation unit 8 is a member (display unit) that is provided in the apparatus main body 2. The display operation unit 8 displays various types of information and receives an input operation for various conditions from the outside. The display operation unit 8 is, for example, a liquid crystal display and displays an operation screen as a touch panel. In this case, an operator can input various conditions through the display operation unit 8. For example, an operation of selecting an image (which will be described in detail below) used by an inspection unit 23 (see FIG. 3) included in the control unit 10 to inspect the article G is received as the input operation. This makes it possible to suitably acquire a desired inspection result.

The control unit 10 is a member to which the detection result of the X-ray detection unit 7 is input and is disposed in the apparatus main body 2. The control unit 10 controls the operation of each unit (in this embodiment, the transport unit 5, the X-ray irradiation unit 6, the X-ray detection unit 7, the display operation unit 8, and the sorting device (not shown) disposed on the downstream side of the X-ray inspection apparatus 1) of the X-ray inspection apparatus 1. In addition, the sorting device is a device that excludes, from a transport path, the object to be inspected (article) which has been determined to be defective in image inspection by the X-ray inspection apparatus 1. A program for controlling the X-ray inspection apparatus 1 is recorded on a ROM.

Figure 3:
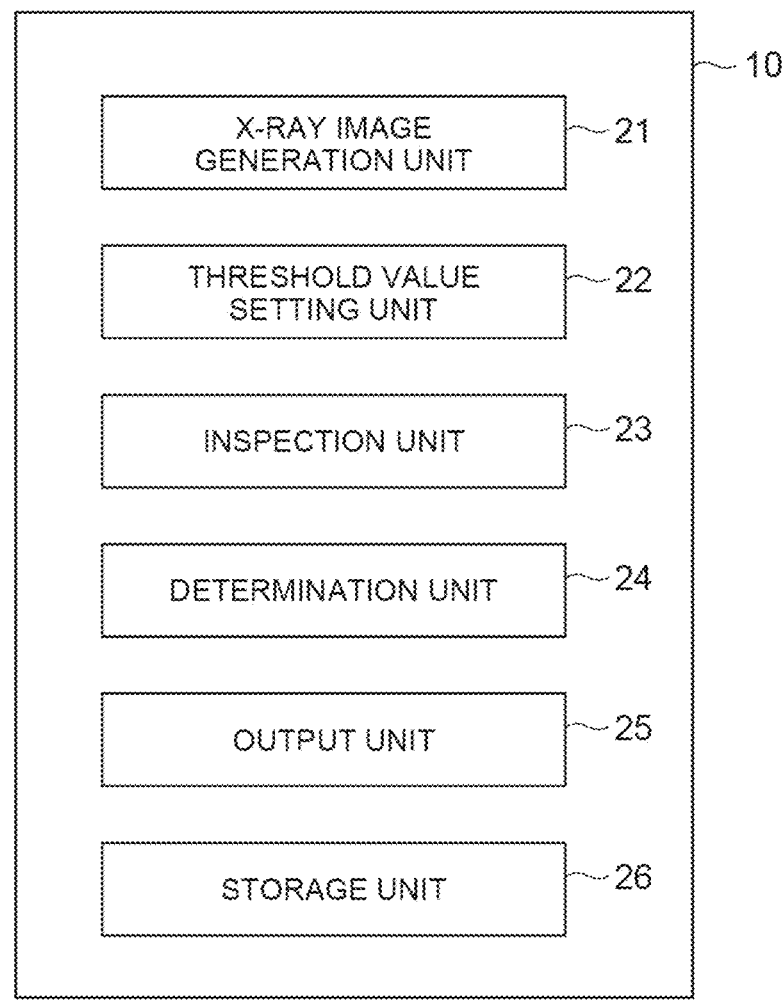
FIG. 3 is a diagram showing a functional configuration of a control unit.

FIG. 3 is a diagram showing a functional configuration of the control unit. As shown in FIG. 3, the control unit 10 includes an X-ray image generation unit 21, a threshold value setting unit 22, the inspection unit 23, a determination unit 24, an output unit 25, and a storage unit 26.

The X-ray image generation unit 21 is a member that expands the signal (for example, the detection result signal) output from the X-ray detection unit 7 into a two-dimensional image on a memory. The X-ray image generation unit 21 is mainly configured by, for example, a graphics processing unit (GPU). The memory on which the two-dimensional image is expanded is, for example, a memory included in the GPU, but is not limited thereto. For example, the X-ray image generation unit 21 generates two or more X-ray transmission images corresponding to two or more energy regions on the basis of the detection result of the X-rays by the X-ray detection unit 7. Each of the X-ray transmission images may be an image used for inspecting the article G (hereinafter, sometimes simply referred to as an "inspection image") or an image for setting the arbitrary threshold value (hereinafter, sometimes simply referred to as a "threshold value setting image"). The inspection image is generated while the article G is being inspected by the X-ray inspection apparatus 1. The threshold value setting image is generated, for example, during the setting of the X-ray inspection apparatus 1 or during the adjustment of the X-ray inspection apparatus 1 (for example, during the calibration of the X-ray inspection apparatus 1). In addition, the X-ray image generation unit 21 may generate, for example, an overall transmission image corresponding to the X-rays in all of a plurality of energy regions as the X-ray transmission image on the basis of the detection result.

Figure 4A:
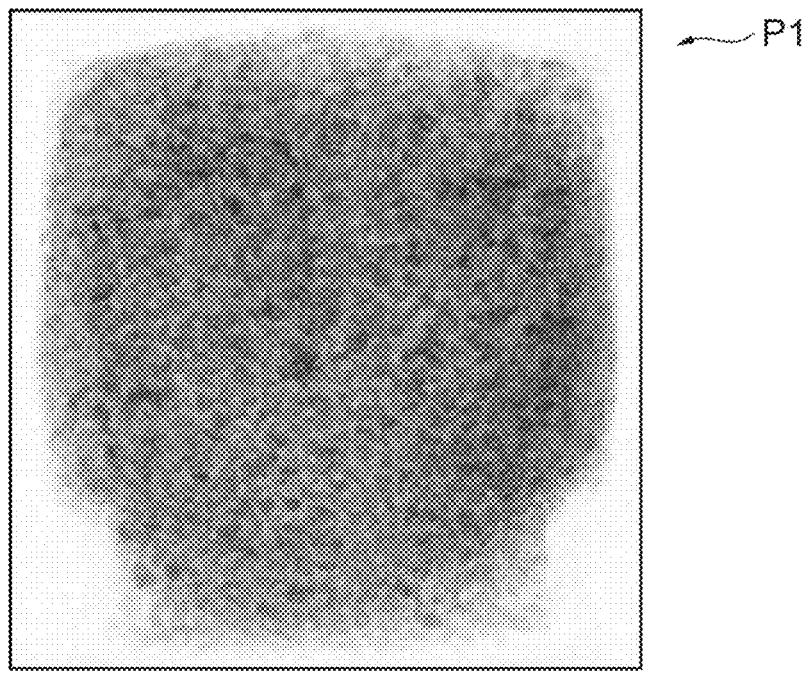
FIG. 4A is a diagram showing a first transmission image.
Figure 4B:
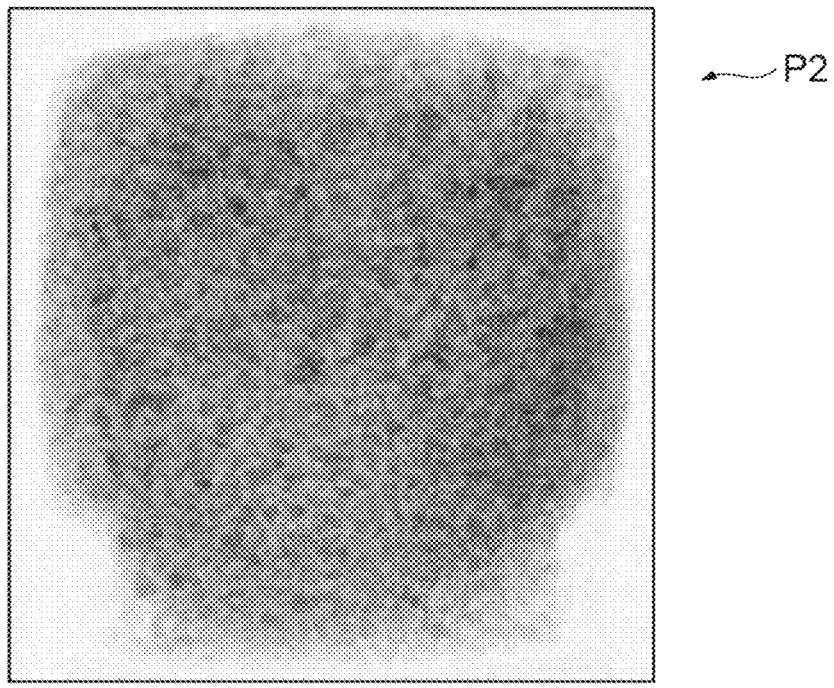
FIG. 4B is a diagram showing a second transmission image.
Figure 5:
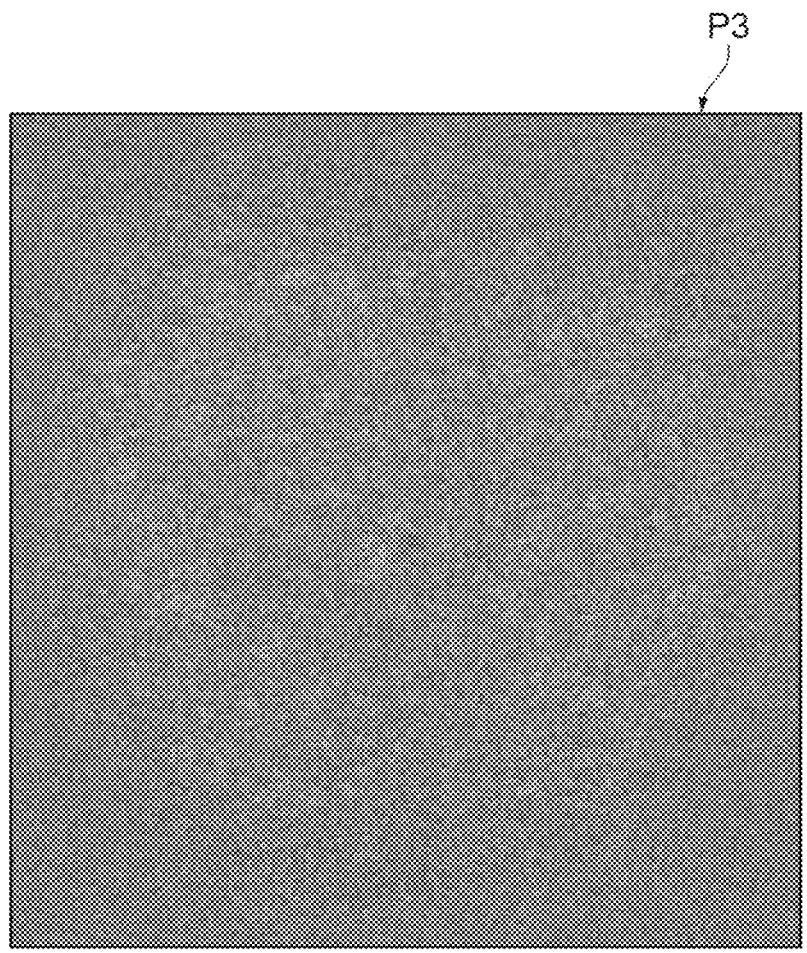
FIG. 5 is a diagram showing a difference image.

In this embodiment, the X-ray image generation unit 21 generates, as the inspection images, a first inspection image P1 (see FIG. 4A) that corresponds to X-rays in the first energy region, a second inspection image P2 (see FIG. 4B) that corresponds to X-rays in the second energy region, and a difference image P3 (see FIG. 5) obtained by a subtraction process between the first inspection image P1 and the second inspection image P2. In addition, the X-ray image generation unit 21 can generate, as the threshold value setting images, a first setting image that corresponds to the X-rays in the first energy region and a second setting image that corresponds to the X-rays in the second energy region.

The first inspection image P1 is generated, for example, on the basis of a portion of information included in the detection result signal. The second inspection image P2 is generated, for example, on the basis of another portion of the information included in the detection result signal. The X-ray image generation unit 21 may generate the first inspection image P1 on the basis of the overall transmission image and the second inspection image P2. In this case, the first inspection image P1 is generated, for example, on the basis of difference data between data used for generating the overall transmission image and data used for generating the second inspection image P2. Alternatively, the X-ray image generation unit 21 may generate the second inspection image P2 on the basis of the overall transmission image and the first inspection image P1. In this case, the second inspection image P2 is generated, for example, on the basis of difference data between the data used for generating the overall transmission image and data used for generating the first inspection image P1. Each of the first inspection image P1 and the second inspection image P2 includes the article G and a background other than the article G. As in the example shown in FIG. 4A, the first inspection image P1 is overall darker than the second inspection image P2. On the other hand, as in the example shown in FIG. 4B, the second inspection image P2 is overall brighter than the first inspection image P1. In this embodiment, the comparison between the brightness of the first inspection image P1 and the brightness of the second inspection image P2 corresponds to the comparison between the brightness of the article G displayed in the first inspection image P1 and the brightness of the article G displayed in the second inspection image P2.

The difference image P3 is, for example, an image (energy analysis image) generated by performing image processing on at least one of the first inspection image P1 and the second inspection image P2 using an image processing algorithm. The image processing algorithm is a type indicating a processing procedure of the image processing performed on at least one of the first inspection image P1 and the second inspection image P2. The image processing algorithm is configured by one image processing filter or a combination of a plurality of image processing filters. A plurality of image processing algorithms can be acquired from the outside through a network such as the Internet. In addition, the plurality of image processing algorithms can also be acquired from an external storage medium such as a USB memory or a removable hard disk. At least one or more of the plurality of image processing algorithms can be automatically generated from a plurality of image processing filters on the basis of, for example, the specifications or inspection conditions of the X-ray inspection apparatus 1, adopting a genetic algorithm (GA) which is a method applying the mechanism of heredity and evolution in the living world. In addition, the operator can appropriately set at least some of the plurality of image processing algorithms through the display operation unit 8. An image processing algorithm used for the first inspection image P1 and an image processing algorithm used for the second inspection image P2 may be different from each other. For example, a process of changing brightness may be performed on one of the first inspection image P1 and the second inspection image P2 in order to match the brightness of the first inspection image P1 with the brightness of the second inspection image P2. As the process, for example, a process using a luminance distribution described in Japanese Patent Application No. 2021-195926, the entire of contents of which are incorporated herein by references, may be performed.

The X-ray image generation unit 21 may use a program that is automatically set by machine learning, instead of using the image processing algorithm. This program is a prediction model (trained model) generated by machine learning and an inference program into which parameters (trained parameters) obtained as a result of machine learning have been incorporated. Examples of the machine learning used for the trained model include a neural network, a support vector machine, and a genetic algorithm. The trained model may include a convolutional neural network or may include a neural network with a plurality of layers (for example, eight or more layers). That is, the trained model corresponding to the above-described program may be generated by deep learning.

The threshold value setting unit 22 is a unit that sets the arbitrary threshold value on the basis of the gradations of two or more X-ray transmission images. The threshold value setting unit 22 sets the arbitrary threshold value on the basis of a threshold value at which a difference between the gradations of the first setting image and the second setting image is within a predetermined range. First, the threshold value setting unit 22 determines a threshold value (temporary threshold value) at which the difference (luminance difference) between the background luminance (first background luminance=B1) of the first setting image and the background luminance (second background luminance=B2) of the second setting image is within a predetermined range. The background luminance of a predetermined X-ray transmission image corresponds to, for example, a value obtained by dividing the total luminance of each pixel included in the image by the number of pixels. In this embodiment, the luminance difference corresponds to a value ($|B2-B1|/(B1+B2)$) obtained by dividing the absolute value ($|B2-B1|$) of the difference between the first background luminance and the second background luminance by the sum ($B1+B2$) of the first background luminance and the second background luminance. In this embodiment, when the luminance difference is equal to or less than 0.05, it is determined that the luminance difference is within a predetermined range. However, the present disclosure is not limited thereto. Then, the threshold value setting unit 22 adds a correction value (unit: keV) to the obtained temporary threshold value to set the arbitrary threshold value. The correction value is an any value that is determined by the operator through the display operation unit 8 and the like. The correction value is, for example, equal to or greater than −10 keV and equal to or less than 10 keV. In addition, the correction value may be 0. That is, the arbitrary threshold value may be the temporary threshold value.

The threshold value setting unit 22 changes the threshold value until the arbitrary threshold value is set (that is, when the difference between the gradations of two or more X-ray transmission images is out of the predetermined range). When the first background luminance is higher than the second background luminance ($B1>B2$), the threshold value setting unit 22 performs correction to decrease the threshold value used previously. When the first background luminance is lower than the second background luminance (B1<B2), the threshold value setting unit 22 performs correction to increase the threshold value used previously. A decreased value and an increased value of the threshold value are not particularly limited. Then, the X-ray image generation unit 21 generates another two or more X-ray transmission images (another first setting image and another second setting image) that correspond to another two or more energy regions classified on the basis of the changed threshold value. Another first setting image and another second setting image are generated after the first setting image and the second setting image. Therefore, hereinafter, each of the first setting image and the second setting image may be referred to as a previous setting image.

When another two or more X-ray transmission images are generated, the threshold value setting unit 22 determines whether or not a difference between gradations of another two or more X-ray transmission images is within a predetermined range. In this embodiment, the threshold value setting unit 22 determines whether or not a difference (another luminance difference) between the background luminance of another first setting image and the background luminance of another second setting image is within a predetermined range. The X-ray image generation unit 21 and the threshold value setting unit 22 repeat the determination of whether or not the difference between the gradations of the first setting image and the second setting image newly generated is within a predetermined range until the arbitrary threshold value is set. Therefore, the threshold value setting unit 22 searches for the arbitrary threshold value. In addition, in the search of the arbitrary threshold value, the threshold value (initial threshold value) that is used first is determined according to, for example, a tube voltage of the X-ray detection unit 7. However, the present disclosure is not limited thereto. The initial threshold value may be, for example, a value that is stored in advance in the storage unit 26.

The threshold value setting unit 22 compares the difference between the gradations of two or more X-ray transmission images with the difference between gradations of another two or more X-ray transmission images. In this embodiment, when another first background luminance is higher than another second background luminance and the first background luminance is lower than the second background luminance, the arbitrary threshold value is set on the basis of the changed threshold value (that is, the search of the threshold value is ended), In addition, when another first background luminance is lower than another second background. Luminance and the first background luminance is higher than the second background luminance, the arbitrary threshold value is set on the basis of the value subjected to the correction of increasing the changed threshold value (that is, the search of the threshold value is ended).

The inspection unit 23 inspects the article G on the basis of the X-rays that have been transmitted through the article G and detected by the X-ray detection unit 7. The inspection unit 23 inspects the article G on the basis of at least some of the plurality of images generated by the X-ray image generation unit 21. The inspection unit 23 inspects the article G using, the example, the difference image P3. In addition, the inspection unit 23 may inspect the article G on the basis of two or more images among the plurality of images generated by the X-ray image generation unit 21. For example, the inspection unit 23 inspects whether a foreign material is present or absent in the article G, whether a crack and a chip are present or absent in the article G, and the like. However, the present disclosure is not limited thereto. For example, when the article G is wrapped in a sheet-like packaging material, the inspection unit 23 can also inspect the tearing of the packaging material, the defective sealing of the packaging material (seal bite), and the like. For example, when the article G is housed in a package, the inspection unit 23 can perform a foreign material confirmation inspection, a missing item confirmation inspection, a number-of-stored-items confirmation inspection, a void confirmation inspection, and the like on the package. The inspection unit 23 transmits the inspection result of the article U to the determination unit 24 and the storage unit 26.

The determination unit 24 determines whether or not the article G is a non-defective article on the basis of the inspection result received from the inspection unit 23. For example, the determination unit 24 determines whether a foreign material is present or absent in the article G, whether a crack and a chip are present or absent in the article G, and the like. The determination unit 24 transmits the determination result to the output unit 25 and the storage unit 26.

The output unit 25 outputs the determination result of the determination unit 24 to at least one of a portion other than the control unit 10 in the X-ray inspection apparatus 1 and an apparatus different from the X-ray inspection apparatus 1. Then, at least one of the X-ray inspection apparatus 1 and the apparatus (for example, the sorting device disposed on the downstream side of the X-ray inspection apparatus 1) different from the X-ray inspection apparatus 1 can perform an operation when the article G is defective. Other examples of the apparatus different from the X-ray inspection apparatus 1 include the carry-in conveyor 51, the carry-out conveyor 52, and a notification device.

The storage unit 26 records signals, data, and the like generated by the control unit 10. For example, the storage unit 26 records the detection result signal transmitted from the X-ray detection unit 7, data of the image transmitted from the X-ray image generation unit 21, data related to the arbitrary threshold value set by the threshold value setting unit, data related to the inspection result transmitted from the inspection unit 23, and data related to the determination result transmitted from the determination unit 24.

Next, a method for adjusting the X-ray inspection apparatus 1 according to this embodiment will be described with reference to FIGS. 6 and 7. The method for adjusting the X-ray inspection apparatus 1 is performed to maintain or improve the inspection accuracy of the X-ray inspection apparatus 1 and is performed, for example, during the calibration of the X-ray inspection apparatus 1. In the following method for adjusting the X-ray inspection apparatus L the arbitrary threshold value used for classifying the photon energy of the detected X-rays is set. Each of FIGS. 6 and 7 is a flowchart showing the method for adjusting the X-ray inspection apparatus.

Figure 6:
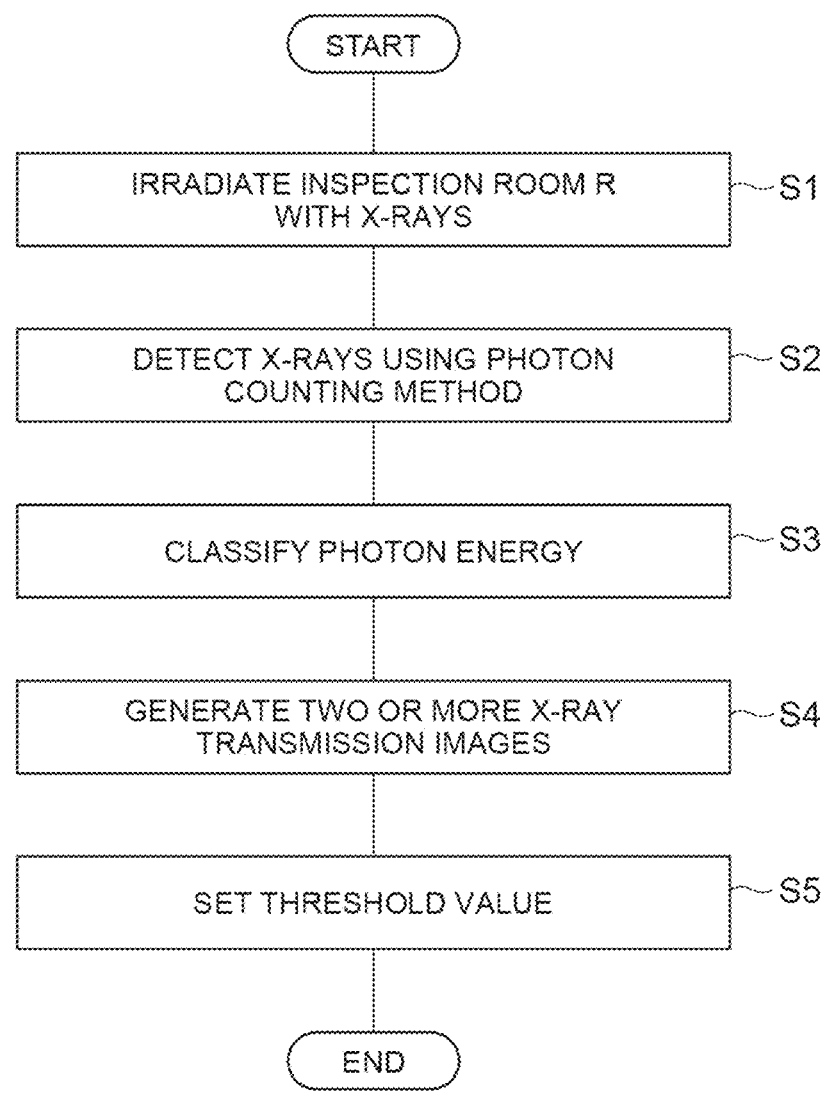
FIG. 6 is a flowchart describing an adjustment method of the X-ray inspection apparatus.
Figure 7:
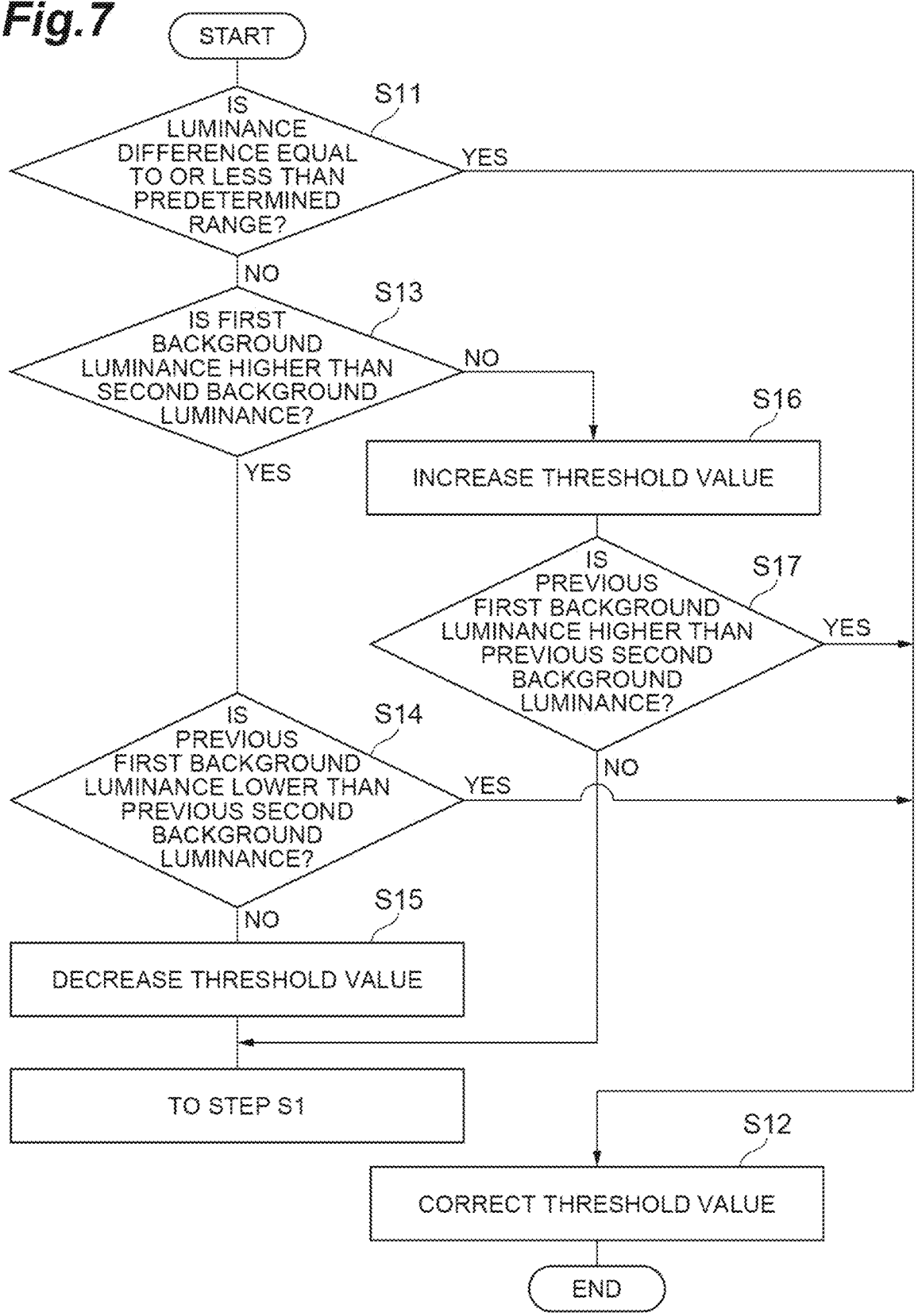
FIG. 7 is a flowchart describing the adjustment method of the X-ray inspection apparatus.

As shown in FIG. 6, first, the inspection room R is irradiated with X-rays (Step S1, an X-ray irradiation step). In Step S1, the X-ray irradiation unit 6 disposed in the shield box 4 is started. Then, the X-rays are detected by the photon counting method (Step S2, an X-ray detection step). In Step S2, the X-ray detection unit 7 detects the X-rays using the photon counting method. Then, the photon energy of the detected X-rays is classified into two or more energy regions by the arbitrary threshold value (Step S3, a classification step). In Step S3, the X-ray detection unit 7 classifies the photon energy into the first energy region and the second energy region using a predetermined initial threshold value.

Then, two or more X-ray transmission images corresponding to two or more energy regions are generated using the photon energy (Step S4, an image generation step). In Step S4, the first setting image is generated from an X-ray detection result corresponding to the first energy region, and the second setting image is generated from an X-ray detection result corresponding to the second energy region.

Then, the arbitrary threshold value is set on the basis of the gradations of the two or more X-ray transmission images (Step S5, a threshold value setting step). In Step S5, a threshold value (temporary threshold value) at which the difference (luminance difference) between the background luminance of the first setting image and the background luminance of the second setting image is within a predetermined range is set. Then, the correction value is added to the obtained temporary threshold value to set the arbitrary threshold value. In addition, when the difference between the gradations of the two or more X-ray transmission images is out of the predetermined range in Step S5, the changing of the threshold value, the classification step, the image generation step, and the threshold value setting step are performed until the difference falls within the predetermined range (that is, Steps S1 to S5 are repeatedly performed). In this case, the photon energy may be classified into another two or more energy regions (second energy regions) on the basis of another threshold value (second or third threshold value) different from the arbitrary threshold value in Step S3, another two or more X-ray transmission images corresponding to another two or more energy regions may be generated in Step S4, and the difference between the gradations of two or more X-ray transmission images may be compared with the difference between gradations of another two or more X-ray transmission images in Step S5.

Here, a method fir setting the arbitrary threshold value will be described in detail with reference to FIG. 7. As shown in FIG. 6, it is determined whether or not the luminance difference is equal to or less than a predetermined range (Step S11). When the luminance difference is equal to or less than the predetermined range (Step S11: YES), the threshold value is corrected (Step S12). In this way, the arbitrary threshold value is set. In addition, the threshold value to be corrected corresponds to the threshold value (for example, the initial threshold value) used in the previous Step S3.

On the other hand, when the luminance difference is out of the predetermined range (Step S11: NO), it is determined whether or not the first background luminance is higher than the second background luminance (Step S13). When the first background luminance is higher than the second background luminance (Step S13: YES), it is determined whether or not the first background luminance (hereinafter, simply referred to as a "previous first background luminance") of the previous first setting image is lower than the second background luminance (hereinafter, simply referred to as a "previous second background luminance") of the previous second setting image (Step S14). When the previous first background luminance is lower than the previous second background luminance (Step S14: YES), Step S12 is performed. On the other hand, when the previous first background luminance is higher than the previous second background luminance (Step S14: NO), the correction of decreasing the threshold value is performed (Step S15). In Step S15, the initial threshold value is decreased by a predetermined value to obtain another threshold value. Then, the process is restarted from Step S1 with another threshold value. When the previous first background luminance and the previous second background luminance are not present, Step S14 is not performed, and Step S15 is performed.

When the first background luminance is lower than the second background luminance (Step S13: NO), the correction of increasing the threshold value is performed (Step S16). In Step S16, the initial threshold value is increased by a predetermined value to obtain another threshold value. Then, it is determined whether or not the previous first background luminance is higher than the previous second background luminance (Step S17). When the previous first background luminance is higher than the previous second background luminance (Step S17: YES), Step S12 is performed. On the other hand, when the previous first background luminance is lower than the previous second background luminance (Step S17: NO), the process is restarted from Step S1 with another threshold value. In addition, when the previous first background luminance and the previous second background luminance are not present, Step S17 is not performed, and Step S1 is performed.

In the X-ray inspection apparatus 1 and the adjustment method thereof according to the above-described embodiment, the threshold value setting unit 22 sets the arbitrary threshold value on the basis of the difference between the gradations of the first setting image and the second setting image. Therefore, for example, when the inspection conditions of the article G are changed, the arbitrary threshold value may be changed. That is, the threshold value setting unit 22 can set an appropriate threshold value corresponding to a change in, for example, inspection conditions, Therefore, even when the inspection conditions of the article G are changed, it is possible to inspect the article G with high accuracy.

In this embodiment, the X-ray detection unit 7 may classify photon energy into the first energy range, the second energy range, and the third energy range lower than the first energy range and the second energy range. In this case, for example, the accuracy of inspecting the article G can be improved by excluding an energy region including the largest amount of noise among the first to third energy regions.

In this embodiment, the arbitrary threshold value is determined on the basis of the temporary threshold value at which the difference between the gradations of the first setting image and the second setting image is within a predetermined range. Therefore, it is easy to find out whether or not a foreign material is present or absent in the article G.

In this embodiment, the arbitrary threshold value is a value obtained by adding the correction value to the temporary threshold value. In this case, it is possible to improve the accuracy of inspecting the article G.

In this embodiment, when the difference between the gradations of the first setting image and the second setting image is out of a predetermined range, the threshold value setting unit 22 may change the arbitrary threshold value, and then the X-ray image generation unit 21 may generate another first setting image and another second setting image corresponding to another two or more energy regions classified on the basis of the changed threshold value. Then, the threshold value setting unit 22 may determine whether or not the difference between the gradations of another first setting image and another second setting image is within a predetermined range. In this case, the threshold value setting unit 22 can accurately set the arbitrary threshold value at which the difference between the gradations of the first setting image and the second setting image is within a predetermined range.

The X-ray image generation unit 21 may generate another first setting image and another second setting image corresponding to another two or more energy regions classified on the basis of another threshold value different from the arbitrary threshold value, and the threshold value setting unit 22 may compare the difference between the gradations of the first setting image and the second setting image with the difference between the gradations of another first setting image and another second setting image. In this case, the threshold value setting unit 22 can easily determine whether or not the arbitrary threshold value is appropriate on the basis of the comparison between the differences.

The embodiment of the present disclosure has been described above. However, the present disclosure is not necessarily limited to the above-described embodiment, and various modifications can be made without departing from the scope of the present disclosure.

Figure 8:
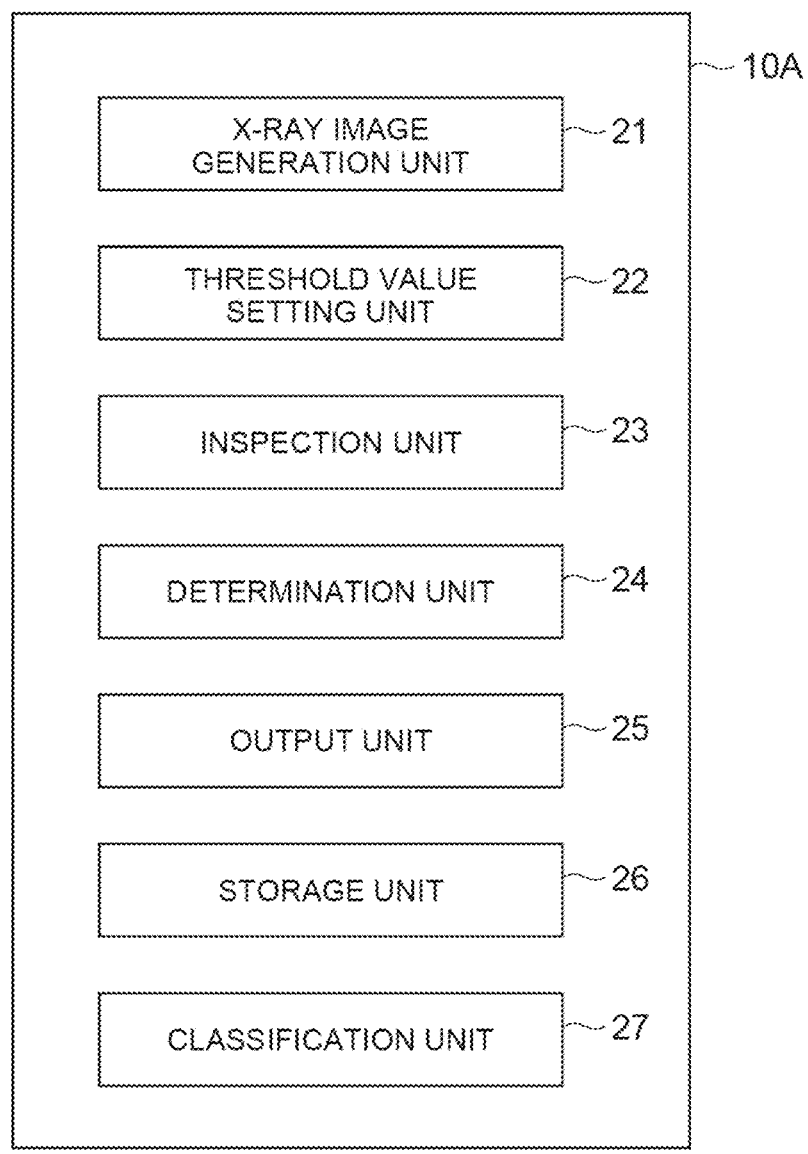
FIG. 8 is a diagram showing a functional configuration of a control unit according to a modification example.

In the above-described embodiment, the X-ray detection unit classifies the photon energy of the detected X-rays into two or more energy regions on the basis of the arbitrary threshold value. However, the present disclosure is not limited thereto. FIG. 8 is a diagram showing a functional configuration of a control unit according to a modification example. As shown in FIG. 8, a control unit 10A includes a classification unit 27, in addition to the X-ray image generation unit 21, the threshold value setting unit 22, the inspection unit 23, the determination unit 24, the output unit 25, and the storage unit 26. The classification unit 27 is a unit that classifies the photon energy of the detected X-rays into two or more energy regions on the basis of the arbitrary threshold value. For example, the classification unit 27 can classify the photon energy into a first energy range, a second energy range, and a third energy range. When the control unit 10A is used, the X-ray detection unit may not perform photon counting for each energy region. In other words, the X-ray detection unit may simply output the detection result of the X-rays to the control unit 10A. This makes it possible to simplify the configuration of the X-ray detection unit.

In the above-described embodiment, the X-ray inspection apparatus has the control unit that performs the image processing. However, the present disclosure is not limited thereto. For example, the function of performing the image processing, the function of determining whether or not a foreign material is present or absent in the article on the basis of the difference image, the function of displaying the X-ray inspection results, and the like in the control unit may not be included in the X-ray inspection apparatus. Alternatively, the functions may be provided in a control device that can perform wired communication or wireless communication with the X-ray inspection apparatus. In this case, it is possible to implement an X-ray inspection system including the X-ray inspection apparatus and the control device to which the inspection results of the X-ray inspection apparatus are input. The same operation and effect as those of the above-described embodiment are also obtained by this X-ray inspection system. In addition, it is possible to simplify the configuration of the control unit provided in the X-ray inspection apparatus. Furthermore, the user can check, for example, the inspection results even at a place away from the X-ray inspection apparatus. Further, the control device is not particularly limited and may be, for example, a laptop PC, a tablet, or the like. In addition, the control device may not have the function of determining whether a foreign material is present or absent.

This application claims the priority benefit of Japanese Application No. 2022-37999 filed on Mar. 11, 2022, the entire contents of which are incorporated herein by references.

What is claimed is:

1. An X-ray inspection apparatus comprising:
a transport unit configured to transport an article;
an X-ray source configured to irradiate the article with X-rays;
an X-ray detection unit configured to detect the X-rays using a photon counting method and to classify photon energy of the detected X-rays into two or more energy regions on the basis of a threshold value;
a threshold value setting unit configured to set the threshold value;
an X-ray image generation unit configured to generate two or more X-ray transmission images corresponding to the two or more energy regions on the basis of a detection result of the X-rays by the X-ray detection unit; and
an inspection unit configured to inspect the article on the basis of the X-rays which have been transmitted through the article and detected by the X-ray detection unit,
wherein the threshold value setting unit is configured to set the threshold value on the basis of gradations of the two or more X-ray transmission images.

2. The X-ray inspection apparatus according to claim 1, wherein the X-ray detection unit is configured to classify the photon energy into a first energy region, a second energy region, and a third energy region lower than the first energy region and the second energy region.

3. The X-ray inspection apparatus according to claim 1, wherein the threshold value is determined on the basis of a second threshold value at which a difference between the gradations of the two or more X-ray transmission images is within a predetermined range.

4. The X-ray inspection apparatus according to claim 3, wherein the threshold value is a value obtained by adding a correction value to the second threshold value.

5. The X-ray inspection apparatus according to claim 1, wherein, when the difference between the gradations of the two or more X-ray transmission images is out of the predetermined range, after the threshold value setting unit changes the threshold value, the X-ray image generation unit is configured to generate two or more second X-ray transmission images corresponding to two or more fourth energy regions classified on the basis of the changed threshold value, and the threshold value setting unit is configured to determine whether or not a difference between gradations of the second X-ray transmission images is within a predetermined range.

6. The X-ray inspection apparatus according to claim 1, wherein the X-ray image generation unit is configured to generate two or more second X-ray transmission images corresponding to two or more fourth energy regions classified on the basis of a third threshold value different from the threshold value, and
the threshold value setting unit is configured to compare the difference between the gradations of the X-ray transmission images with a difference between gradations of the second X-ray transmission images.

7. An X-ray inspection apparatus comprising:
a transport unit configured to transport an article;
an X-ray source configured to irradiate the article with X-rays;

an X-ray detection unit configured to detect the X-rays using a photon counting method; and a control unit to which a detection result of the X-ray detection unit is input, wherein the control unit includes:

a classification unit configured to classify photon energy of the X-rays detected by the X-ray detection unit into two or more energy regions on the basis of a threshold value;

a threshold value setting unit configured to set the threshold value;

an X-ray image generation unit configured to generate two or more X-ray transmission images corresponding to the two or more energy regions on the basis of the detection result of the X-rays by the X-ray detection unit; and an inspection unit configured to inspect the article on the basis of the X-rays which have been transmitted through the article and detected by the X-ray detection unit, and the threshold value setting unit is configured to set the threshold value on the basis of gradations of the two or more X-ray transmission images.

8. The X-ray inspection apparatus according to claim 7, wherein the classification unit is configured to classify the photon energy into a first energy region, a second energy region, and a third energy region lower than the first energy region and the second energy region.

9. The X-ray inspection apparatus according to claim 7, wherein the threshold value is determined on the basis of a second threshold value at which a difference between the gradations of the two or more X-ray transmission images is within a predetermined range.

10. The X-ray inspection apparatus according to claim 9, wherein the threshold value is a value obtained by adding a correction value to the second threshold value.

11. The X-ray inspection apparatus according to claim 7, wherein, when the difference between the gradations of the two or more X-ray transmission images is out of the predetermined range, after the threshold value setting unit changes the threshold value, the X-ray image generation unit is configured to generate two or more second X-ray transmission images corresponding to two or more fourth energy regions classified on the basis of the changed threshold value, and the threshold value setting unit is configured to determine whether or not a difference between gradations of the second X-ray transmission images is within a predetermined range.

12. The X-ray inspection apparatus according to claim 7, wherein the X-ray image generation unit is configured to generate two or more second X-ray transmission images corresponding to two or more fourth energy regions classified on the basis of a third threshold value different from the threshold value, and the threshold value setting unit is configured to compare the difference between the gradations of the X-ray transmission images with a difference between gradations of the second X-ray transmission images.

13. An adjustment method of an X-ray inspection apparatus, the adjustment method comprising:

an X-ray irradiation step of irradiating an inspection room provided in a housing with X-rays;

an X-ray detection step of detecting the X-rays using a photon counting method;

a classification step of classifying photon energy of the detected X-rays into two or more energy regions on the basis of a threshold value;

an image generation step of generating two or more X-ray transmission images corresponding to the two or more energy regions, using the photon energy; and a threshold value setting step of setting the threshold value on the basis of gradations of the two or more X-ray transmission images.

14. The adjustment method according to claim 13, wherein, when a difference between the gradations of the two or more X-ray transmission images is out of a predetermined range in the threshold value setting step, a change of the threshold value, the classification step, the image generation step, and the threshold value setting step are performed until the difference falls within the predetermined range.

15. The adjustment method according to claim 13, wherein, in the classification step, the photon energy is classified into two or more second energy regions on the basis of second threshold values different from the threshold value, in the image generation step, two or more second X-ray transmission images corresponding to the second energy regions are generated, and in the threshold value setting step, a difference between the gradations of the X-ray transmission images is compared with a difference between gradations of the second X-ray transmission images.

* * * * *